United States Patent
Yang et al.

(10) Patent No.: US 11,805,782 B2
(45) Date of Patent: Nov. 7, 2023

(54) BIOCONTROL STRAIN YW-1 AND PREPARATION METHOD AND APPLICATION OF BIOCONTROL AGENT THEREOF

(71) Applicant: Huaiyin Normal University, Huai'an (CN)

(72) Inventors: Wei Yang, Huai'an (CN); Haixia Yan, Huai'an (CN); Guanghui Dong, Huai'an (CN); Yusheng Qiu, Huai'an (CN); Yuelong Zhu, Huai'an (CN); Zi Zhang, Huai'an (CN); Wei Guo, Huai'an (CN); Shimo Li, Huai'an (CN); Lei Zhang, Zhenjiang (CN); Yuming Luo, Huai'an (CN)

(73) Assignee: HUAIYIN NORMAL UNIVERSITY, Huai'an (CN)

( * ) Notice: Subject to any disclaimer, the term of this patent is extended or adjusted under 35 U.S.C. 154(b) by 121 days.

(21) Appl. No.: 17/523,064

(22) Filed: Nov. 10, 2021

(65) Prior Publication Data
US 2022/0142171 A1    May 12, 2022

Related U.S. Application Data

(63) Continuation of application No. PCT/CN2020/129982, filed on Nov. 19, 2020.

(30) Foreign Application Priority Data

Nov. 6, 2020   (CN) .......................... 202011229617.2

(51) Int. Cl.
| | |
|---|---|
| *A01N 63/20* | (2020.01) |
| *C12N 1/20* | (2006.01) |
| *A01P 3/00* | (2006.01) |
| *A01P 1/00* | (2006.01) |
| *C12R 1/01* | (2006.01) |

(52) U.S. Cl.
CPC ............. *A01N 63/20* (2020.01); *A01P 1/00* (2021.08); *A01P 3/00* (2021.08); *C12N 1/205* (2021.05); *C12R 2001/01* (2021.05)

(58) Field of Classification Search
CPC .......... A01N 63/20; C12N 1/205; C12N 1/20; C12R 2001/01; C12R 2001/20
See application file for complete search history.

(56) References Cited

FOREIGN PATENT DOCUMENTS

CN          102146350 A        8/2011

OTHER PUBLICATIONS

Dictionary.com "Thallus Definition & Meaning" 5 pages, May 6, 2023 (Year: 2023).*
Machine translation of CN102146350A, 5 pgs May 6, 2023 (Year: 2023).*

* cited by examiner

*Primary Examiner* — Thane Underdahl
(74) *Attorney, Agent, or Firm* — Rachel K. Pilloff; Sean A. Passino; Pilloff Passino & Cosenza LLP

(57) ABSTRACT

A biocontrol strain YW-1, a preparation method and application of a biocontrol agent thereof are provided. The strain is *Myroides odoratimimus* with the preservation number of CGMCC NO. 20620. The biocontrol agent of the biocontrol strain YW-1 is obtained by the following steps: oscillating culture the biocontrol strain YW-1 in a LB culture medium at 30 Celsius degrees and 180 rpm for 12-16 hours until a total concentration of living bacteria in a bacterial suspension is $1\times10^9$-$1\times10^{10}$ CFU/mL; centrifuging the bacterial suspension at 6000 rpm for 10 minutes to collect bacterial cells; and diluting the bacterial cells with sterilized water to obtain a concentration of 100 CFU/milliliter. By irrigating the root of every plant with 20 milliliters of the biocontrol agent when host plants are transplanted, it can effectively prevent soil-borne diseases such as *fusarium* wilt of melons, bacterial wilt of tomatoes and peppers, and *Phytophthora capsici*.

3 Claims, 2 Drawing Sheets
Specification includes a Sequence Listing.

BIOCONTROL STRAIN YW-1 AND PREPARATION METHOD AND APPLICATION OF BIOCONTROL AGENT THEREOF

TECHNICAL FIELD

The invention belongs to the technical field of plant protection, and particularly relates to preparation and application of a biocontrol strain YW-1 and a biocontrol agent thereof.

BACKGROUND

Protected agriculture is a modern agricultural production way, which integrates applied engineering equipment technology, biotechnology and environmental technology, provides agreeable environment for the growth and development of animals and plants, and realizes animal and plant production. The development of protected vegetable not only alleviates the contradiction between seasonal production and balanced consumption, but also makes use of facilities to cultivate and produce high-grade vegetables, brand and quality vegetables and seasonal vegetables, and increases the variety of vegetables to meet the consumption needs of people of different living standards. China has become the country with the largest facility area in the world, which is still growing at an annual rate of about 10%.

However, since the production of protected vegetables, there are still some problems that can't be ignored. Protected vegetable cultivation has the disadvantages like frequent soil cultivation, high intensification, high multiple cropping index and single species. Continuous cropping obstacles such as soil deterioration, frequent diseases and insect pests, and inferior quality generally occur, which seriously affect the production of vegetables and cut down farmers' income. After analyzing the protected cultivation under various conditions, many scholars at home and abroad hold the opinion that soil-borne diseases and insect pests are the main barrier for continuous cropping.

In protected cultivation, the pathogens of vegetable diseases and insect pests often lurk in the soil, such as *fusarium* wilt and epidemic disease of cucumbers and eggplants, and their spores often overwinter in the soil, which will continue to be harmful in the coming year. In addition, the temperature and humidity in the greenhouse are high, and such climatic conditions are conducive for the occurrence and mutual transmission of vegetable diseases and insect pests, which is harmful to vegetables and easy to form a vicious circle. With the increase of continuous cropping years, the species and quantity of harmful fungi increases, while the antagonistic bacteria against pathogenic bacteria in soil decreases, which further aggravates soil-borne diseases. For the prevention and control of soil-borne diseases, various prevention and control approaches have been accumulated in practice, including grafting, soil disinfecting, increasing application of organic fertilizer, and biological control, etc. Among them, using soil antagonistic microorganisms to control soil-borne diseases can not only be carried out in situ, but also be harmless to humans and animals and friendly to the environment, which has attracted growing attention from scholars. However, the biggest obstacle hindering the development of biological control at present is the limited scope of control and the unstable effect of field biological control. Among them, the single action mode of biocontrol strains on pathogens and their inability to adapt to the field environment are the most important factors. Therefore, screened biocontrol strains with various mechanisms, broad range of action and strong adaptability will have greater application potential and prospects.

SUMMARY

In view of the problems of single action mode and small control scope of biocontrol strains for soil-borne diseases of plants at present, the invention provides biocontrol strain YW-1 and a preparation method and application of the biocontrol agents thereof by screening the activity of various metabolites and testing the bacteriostatic activity.

To achieve the above objective, the invention provides the following scheme.

The invention provides a biocontrol strain YW-1 *Myroides odoratimimus*, and the preservation number of the strain is CGMCC NO. 20620.

The invention provides a biocontrol agent prepared by utilizing the biocontrol strain YW-1.

The invention provides a preparation method of the biocontrol agent, which comprises the following steps: culturing the biocontrol strain YW-1 in LB culture medium, and then collecting the strain and diluting with sterilized water to prepare the biocontrol agent with a final concentration of $1 \times 10^7$ colony-forming units per milliliter (CFU/mL).

Preferably, a bacterial suspension is obtained after culturing the biocontrol strain YW-1 in LB culture medium, the bacterial suspension has an initial concentration of viable bacteria of $1 \times 10^9$-$1 \times 10^{10}$ CFU/mL.

The invention also provides an application of the biocontrol agent prepared by the biocontrol strain in preventing and controlling soil-borne diseases of plants.

Preferably, the soil-borne diseases of plants are one or more of *Fusarium* wilt of melons, bacterial wilt of tomatoes and peppers and *Phytophthora capsici*.

The invention discloses the following technical effects.

the advantages and positive effects of the invention are as follows: the invention specifically screens various common soil-borne diseases of plants, and has better prevention and control effects on common soil-borne diseases including *Fusarium* wilt, bacterial wilt and epidemic disease by screening activities of various metabolites, so the invention overcomes the defect of single disease prevention and control by previous biocontrol strains, and has greater practical application potential and application range.

The experiment operated in greenhouse shows that when the host plants are transplanted, 20 mL of the biocontrol agent is irrigated to each of the roots of the plants, which could effectively control many soil-borne diseases such as *Fusarium* wilt of melons, bacterial wilt of tomatoes and peppers, and *Phytophthora capsici*. Compared with the blank control group, the control effect is over 50%.

BRIEF DESCRIPTION OF DRAWINGS

FIG. 2A is antagonistic screening of *Ralstonia solanacearum*, in which strain 21 is YW-1; FIG. 2B and FIG. 2C are antagonistic screening of *Fusarium* wilt and *Phytophthora infestans*, in which linear colonies are antagonistic bacterial colonies, circular colonies in FIG. 2B are *Fusarium* wilt to be detected, and circular colonies in FIG. 2C are *Phytophthora infestans* to be detected; among them, YW-1 strain is No. 21 in the linear colony, and the strains in other linear cannot meet the screening conditions.

DETAILED DESCRIPTION OF EMBODIMENTS

Figure 1A:
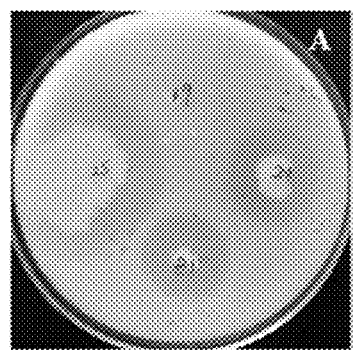
FIG. 1A through FIG. 1C show the screening result of metabolite activity of strain YW-1; among them, A, B and C are chitinase, cellulase and siderophore activity detection plates, in which strain No. 21 is YW-1, and other strains do not meet the screening conditions.

Embodiments of the invention will be further explained with reference to the accompanying figures. The detailed descriptions should not be regarded as limitations of the invention, but should be understood as more detailed descriptions of certain aspects, characteristics and embodiments of the invention.

It should be understood that the terms described in the invention are only for describing specific embodiments, rather than limiting the invention. In addition, as for the numerical range in the invention, it should be understood that every intermediate value between the upper limit and the lower limit of the range is also specifically disclosed. Intermediate values within any stated value or stated range and every smaller range between any other stated value or intermediate values within the stated range are also included in the invention. The upper and lower limits of these smaller ranges can be independently included or excluded from the range.

Unless otherwise stated, all technical and scientific terms used herein have the same meanings as commonly understood by those of ordinary skill in the art to which this invention relates. Although the invention only describes preferred methods and materials, any methods and materials similar or equivalent to those described herein may be used in the practice or testing of the invention. All documents mentioned in this specification are incorporated by reference to disclose and describe methods and/or materials related to the documents. In case of conflict with any incorporated documents, the contents of this specification shall prevail.

Without departing from the scope or spirit of the invention, it is obvious to those skilled in the art that many modifications and changes can be made to the specific embodiments of the specification of the invention. Other embodiments derived from the description of the invention will be apparent to the skilled person. The specification and examples of this application are only exemplary.

As used herein, "include", "contain", "have", "comprise", etc. are all open terms, which means including but not limited to.

Example 1

The invention relates to a biocontrol strain YW-1 called *Myroides odoratimimus* for preventing and controlling soil-borne diseases of various plants, which was isolated from the soil of pepper greenhouse in Wudun Town, Huai'an City, Jiangsu Province in 2015. The *Myroides odoratimimus* was preserved in the General Microbiology Center of China Microbiological Collection Management Committee on Sep. 9, 2020 (the address is No. 3, No. 1 Courtyard, Beichen West Road, Chaoyang District, Beijing City, Institute of Microbiology, Chinese Academy of Sciences), and the strain preservation number is CGMCC NO. 20620.

1. Isolation and Purification of Biocontrol Strain YW-1

(1) Dig the soil at the root of the plant to a depth of 10 cm, then collect the soil attached on the surface of the plant root with a small brush, put the soil into a small self-sealing bag, mark it with a number, and quickly bring it back to the laboratory for further study.

(2) In this study, LB medium is used to separate the strains by spreading plate method: taking 1 g of each soil sample and dissolving the samples in 9 mL of sterile water respectively, and then diluting each group to $10^{-3}$, $10^{-4}$ and $10^{-5}$ in concentration respectively; taking 100 mL of the culture medium respectively onto the culture mediums and spraying, following by 3 times of repeating for each gradient. After labeled, the mediums are placed in a greenhouse incubator at 28° C. for cultivation. After the colony grows, the strains with fine shape are selected and purified, and then stored at −70° C. for later use.

2. Identification of Biocontrol Strain YW-1

(1) Microbiological characteristics: after strain YW-1 is cultured on LB medium at 28° C. for 48 h, colonies with a diameter of 1.5 mm grow on the surface of the medium, which has full colonies in light yellow, wet and shiny surface, and smooth edge.

(2) Molecular biological characteristics: the genomic DNA of strain YW-1 is extracted with the resin genomic kit (Shanghai Saibaisheng Gene Technology Co., Ltd.). The 16s rDNA fragment is amplified with 16s universal primers with the extracted genomic DNA as template, and then sequenced (Nanjing GenScript Biotechnology Co., Ltd.). The sequencing results are submitted to NCBI database for comparison, and the comparison results show that the similarity with *Myroides odoratimimus* PR63039 (Accession: CP013690.1) reaches 99%. The 16s rDNA sequence of strain YW-1 is shown in SEQ ID No. 1.

3. Screening of Metabolite Activity of Biocontrol Strain YW-1

Figure 1B:
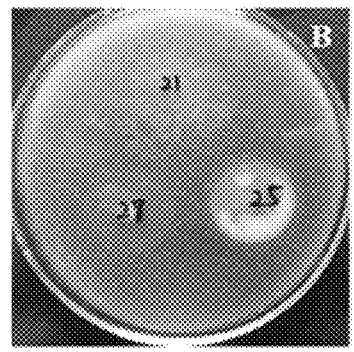
Figure 1C:
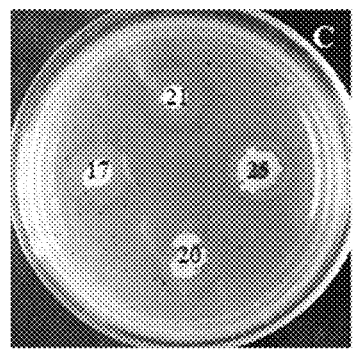

The screening of metabolite activity of this strain includes chitinase activity, cellulase activity and siderophore activity. Table 1 and FIG. 1A through FIG. 1C are screening results of metabolite activity of strain YW-1, among which A, B and C are chitinase, cellulase and siderophore activity detection plates, and strain No. 21 is YW-1. The specific screening methods are as follows:

Detection of Chitinase-producing activity: the strain is cultured on the culture medium with colloidal chitin as the sole carbon source: (the medium contains $NH_4H_2PO_4$ 1.0 g, KCl 0.2 g, $MgSO_4 \cdot 7H_2O$ 0.2 g, colloidal chitin 1% (w/v) to a constant volume of 1000 mL, pH=7.0 and agar 20 g); after inoculation, the strain is cultured at 30° C. for 3 days, and the size of transparent circle is measured. Strains with hydrolysis circle radius (difference between outer diameter and inner diameter) larger than 5 mm are considered to have significant Chitinase activity.

Detection of Cellulase-producing activity: the strain is cultured on a cellulase activity determination plate (the plate contains peptone 10 g, yeast powder 10 g, sodium carboxymethyl cellulose 10 g, sodium chloride 5 g, potassium dihydrogen phosphate 1 g, agar 18 g, fix to 1000 mL and pH=7.0) at 30° C. for 48 h, then dyed with Congo red 1 g/L for 1 hour, and then the dye solution is removed and soaked in 1M of NaCl. Measuring the size of the transparent circle, and selecting strains with hydrolysis circle radius (difference between outer diameter and inner diameter) larger than 5 mm as having significant cellulase activity.

Detection of siderophore-producing activity: solution A: (1) dissolve 60.5 mg of CAS (chrome azurol S) in 50 mL of deionized water; (2) prepare 10 mL of ferric iron solution (take 1 mm of $FeCl_3 \cdot 6H_2O$ and 10 mm of hydrochloric acid as solvent); (3) dissolve 72.9 mg of HDTMA in 40 mL of deionized water. The above three solutions are mixed to a constant volume of 100 mL, and the pH is adjusted to neutrality, and sterilized at 121° C. for 20 min Solution B: 30.24 g of pipes are added to 900 mL of WA culture medium, the pH is adjusted to 6.8, and the solution is sterilized at 121° C. for 20 min. A and B solutions are mixed and poured into a flat plate, and then cultured at 30° C. for 3 days for observation. The size of the transparent circle is measured, and the strains with hydrolysis circle radius (difference between outer diameter and inner diameter) greater than 5 mm are detected as having significant iron-producing activity.

TABLE 1

Screening results of metabolite activity of strain YW-1

| Detection of activity Item | Detection of Chitinase activity | | Detection of Cellulase activity | | Detection of Ciderophore-producing activity | |
|---|---|---|---|---|---|---|
| | Inner diameter (mm) | Outer diameter (mm) | Inner diameter (mm) | Outer diameter (mm) | Inner diameter (mm) | Outer diameter (mm) |
| YW-1 | 3 | 12 | 5 | 11 | 3 | 12 |

Remarks: The inner diameter is the diameter of colony formed by the growth of strain on the plate, and the outer diameter is the diameter of hydrolysis circle formed, all of which are in millimeters (mm).

4. Detection of Bacteriostatic Activity of Biocontrol Strain YW-1 on Plate

Figure 2A:
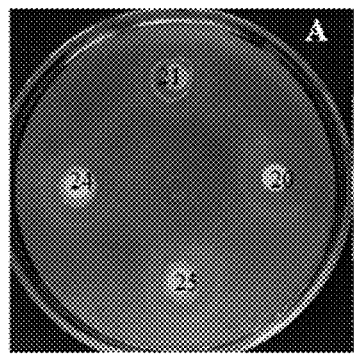
FIG. 2A through FIG. 2C show the screening result of antagonistic activity of strain YW-1.
Figure 2B:
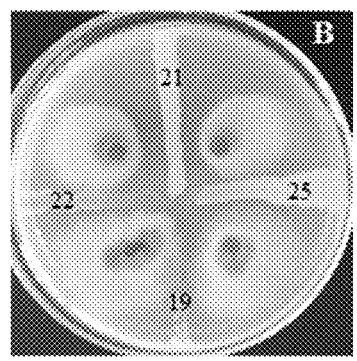
Figure 2C:
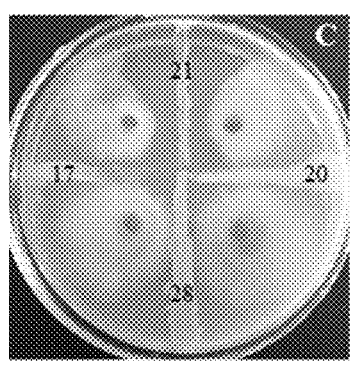

The plate inhibition activity of biological control strain YW-1 against *Fusarium* wilt, bacterial wilt and epidemic disease pathogen is detected by plate confrontation growth method. Table 2 shows the plate inhibition activity detection of strain YW-1, and FIG. 2A through FIG. 2C show the screening result of plate antagonism activity of strain YW-1. FIG. 2A antagonistic screening of *Ralstonia solanacearum*, in which strain 21 is YW-1; FIG. 2B and FIG. 2C are antagonistic screening of *Fusarium* wilt and *Phytophthora infestans*, in which linear colonies are antagonistic bacterial colonies, circular colonies in FIG. 2B are *Fusarium* wilt to be tested, and circular colonies in FIG. 2C are *Phytophthora infestans* to be tested, in which No. 21 in linear colonies is YW-1 strain, and strains in other linear colonies are strains that do not meet the screening conditions. Specific methods are as follows.

Bacteriostatic activity detection of *Ralstonia solanacearum*: after culturing *Ralstonia solanacearum* on YGPA plate for 2 days, the bacteria are collected and suspended in sterile water to prepare bacterial suspension with $OD_{600}$=0.2 (2.0×108 CFU/mL). Add 5 mL of bacterial suspension and 2 mL of (5%) TZC to 400 mL of YGPA culture medium at 45° C., mix well, and invert the plate. Activate biocontrol bacteria strains with LB plate, pick the colonies in the peak growth period with toothpicks and spot them on YGPA plate containing bacterial wilt pathogen, which has 5 spots on each plate with the same spacing, and culture them at 30° C. for 48 h, observe and record the results, measure the inner diameter of the antagonistic bacteria and the outer diameter of the antagonistic ring respectively, and select the strains with the radius of antagonistic ring (difference between outer diameter and inner diameter) greater than 5 mm as having significant inhibitory activity on *Ralstonia solanacearum*.

Detection of Antibacterial Activity of *Fusarium* Wilt and Epidemic Disease:

*Phytophthora* and *Fusarium* wilt stored at 4° C. are inoculated on PDA plate for activation by the method of confrontation culture; after the fungi grow up on the plate, they are evenly punched into round pieces with a diameter of 8 mm from the outer edge of the colony with a sterilized punch; the mycelial pieces are evenly inoculated in four directions of WA plate with the interval of 2 cm; after culture for 24 h, the bacteria to be tested are divided between two hyphal blocks by the method of streaking inoculation. Culture the bacteria at 25° C. for 36-48 h, record the size of the bacteriostatic radius, and select strains with antagonistic circle radius (difference between outer diameter and inner diameter) greater than 5 mm as having significant bacteriostatic activity.

TABLE 2

| Bacteria | Ralstonia solanacearum | | Fusarium wilt | | Phytophthora | |
|---|---|---|---|---|---|---|
| | Inner diameter (mm) | Inner diameter (mm) | Inner diameter (mm) | Inner diameter (mm) | Inner diameter (mm) | Inner diameter (mm) |
| YW-1 | 6 | 11 | 4 | 15 | 3 | 15 |

Example 2

Preparation of YW-1 Biocontrol Agent

The biocontrol strain YW-1 is cultured in LB culture medium (which contains tryptone 10 g/L, yeast extract 5 g/L, sodium chloride 10 g/L, pH=7.2) at 28° C. at 180 revolutions per minute (rpm) for 12-16 h, and then the concentration of viable bacteria is $1×10^9$-$1×10^{10}$ CFU/mL; then the bacterial suspension is centrifuged at 6000 rpm for 10 min to collect the bacteria, and diluted with sterilized water to prepare a biocontrol agent with a concentration of $1×10^7$ CFU/mL.

Example 3

Verification of the Control Effect of YW-1 Biocontrol Agent on Many Soil-Borne Diseases of Plants in Greenhouse Pots 1. The greenhouse pot experiment is conducted to detect the control effect of YW-1 biocontrol agent on tomato and pepper bacterial wilt.

Tomato seedlings and pepper seedlings are cultivated in plug trays, and transplanted when they have 3-4 true leaves. In the treatment group, 20 mL of $1×10^7$ CFU/mL bacterial agent is used for root irrigation, while the control group is treated with clear water. One week after transplantation, 20 mL of *Ralstonia solanacearum* 3721 suspension is inoculated. There are 24 plants in each treatment group, and the treatment is repeated for three times. Under the conditions of temperature 25-28° C., relative humidity 60% and illumination 12 h/12 h, the plants are cultured for 4 weeks; then the disease degree is investigated, and the disease severity and control effects are calculated.

According to the disease classification standard proposed by Kempe and Sequeria in 1983, the calculation formula of disease severity and control effect is as follows:

DI 0, no disease;

DI 1, ≤25% of the leaves are wilted;

DI 2, 25-50% of the leaves are wilted;

DI 3, 50-75% of the leaves are wilted;

DI 4, 75-100% of the leaves are wilted (Kempe and Sequeria, 1983).

Disease severity =

$$\frac{\sum(\text{number of plants with } diease \times \text{degree of } diease)}{\text{number of total plants} \times \text{highest degree of } deiase} \times 100\%$$

$$\text{Control effect} = \frac{\text{Disease severity of control group} - \text{disease severity of treatment group}}{\text{Disease severity of control group}} \times 100\%$$

The results of investigation after transplanting for 4 weeks (as shown in Table 3 and Table 4) show that the control effect of biological control agent YW-1 on tomato bacterial wilt reaches 59.68%, and that on pepper bacterial wilt reaches 62.48%.

TABLE 3

Biocontrol effect of biocontrol agent YW-1 on tomato bacterial wilt in greenhouse

| Treatment | Disease severity (%) | Biocontrol effect (%) |
|---|---|---|
| YW-1 | 28.33 ± 1.67b | 59.68 |
| Control | 70.28 ± 0.28a | 0 |

TABLE 4

Biocontrol Effect of Biocontrol Agent YW-1 on Pepper Bacterial Wilt in Greenhouse

| Treatment | Disease severity (%) | Biocontrol effect (%) |
|---|---|---|
| YW-1 | 27.45 ± 0.89b | 62.48 |
| Control | 73.16 ± 0.54a | 0 |

2. The greenhouse pot experiment is used to detect the control effect of YW-1 biocontrol agent on cucumber *Fusarium* wilt.

Cucumber seedlings are cultivated in plug trays, and transplanted when they have 3-4 true leaves. The treatment group is treated with 20 mL of 1×10$^7$ CFU/mL biocontrol agent while the control group is treated with clear water. One week after transplanting, 20 mL of 10$^5$ sporangium/mL *Fusarium* wilt pathogen suspension is inoculated. There are 24 plants in each treatment group and the operation is repeated for three times. Under the conditions of temperature 25-28° C., relative humidity 60% and illumination 12 h/12 h, the plants are cultured for 3 weeks; then the disease degree is investigated, and the disease severity and control effect is calculated.

According to the disease classification standard proposed by Kempe and Sequeria in 1983, the calculation formula of disease severity and control effect is as follows:

DI 0, no disease;
DI 1, ≤25% of the leaves are wilted;
DI 2, 25-50% of the leaves are wilted;
DI 3, 50-75% of the leaves are wilted;
DI 4, 75-100% of the leaves are wilted (Kempe and Sequeria, 1983).

Disease severity =

$$\frac{\sum(\text{number of plants with } diease \times \text{degree of } diease)}{\text{number of total plants} \times \text{highest degree of } deiase} \times 100\%$$

$$\text{Control effect} = \frac{\text{Disease severity of control group} - \text{disease severity of treatment group}}{\text{Disease severity of control group}} \times 100\%$$

3 weeks after transplanting, the results show that the control effect of biological control agent YW-1 on cucumber *Fusarium* wilt reaches 64.80% (as shown in Table 5).

TABLE 5

Biocontrol effect of biocontrol agent YW-1 on cucumber Fusarium wilt in greenhouse

| Treatment | Disease severity (%) | Biocontrol effect (%) |
|---|---|---|
| YW-1 | 24.31 ± 0.67b | 64.80 |
| Control | 69.08 ± 0.32a | 0 |

3. The Greenhouse Pot Test is Used to Detect the Control Effect of YW-1 Biocontrol Agent on Pepper Blight.

Pepper seedlings are cultivated in plug trays, and transplanted when they have 3-4 true leaves. The treatment group is treated with 20 mL of 1×10$^7$ CFU/mL biocontrol agent for root irrigation, while the control group is treated with clear water. One week after transplantation, 20 mL of *Phytophthora infestans* suspension with 10$^5$ sporangium/mL is inoculated. There are 24 plants in each treatment group and the operation is repeated for three times. Under the conditions of temperature 25-28° C., relative humidity 60% and illumination 12 h/12 h, the plants are cultivated for 4 weeks; then the disease degree is investigated, and the disease severity and control effect is calculated.

According to the disease classification standard proposed by Kempe and Sequeria in 1983, the calculation formula of disease severity and control effect is as follows:

DI 0, no disease;
DI 1, ≤25% of the leaves are wilted;
DI 2, 25-50% of the leaves are wilted;
DI 3, 50-75% of the leaves are wilted;
DI 4, 75-100% of the leaves are wilted (Kempe and Sequeria, 1983).

Disease severity =

$$\frac{\sum(\text{number of plants with } diease \times \text{degree of } diease)}{\text{number of total plants} \times \text{highest degree of } deiase} \times 100\%$$

$$\text{Control effect} = \frac{\text{Disease severity of control group} - \text{disease severity of treatment group}}{\text{Disease severity of control group}} \times 100\%$$

The investigation results after transplanting for 4 weeks (as shown in Table 6) show that the control effect of biological control agent YW-1 on pepper blight reaches 71.36%.

TABLE 6

Biocontrol Effect of Biocontrol Agent YW-1 on Pepper Phytophthora blight in Greenhouse

| Treatment | Disease severity (%) | Biocontrol effect (%) |
|---|---|---|
| YW-1 | 20.37 ± 0.94b | 71.36 |
| Control | 71.12 ± 0.53a | 0 |

The greenhouse experiment shows that when the host plants are transplanted, 20 mL/plant is irrigated with the biocontrol agent, which could effectively control many soil-borne diseases such as *Fusarium* wilt of melons, bacterial wilt of tomatoes and peppers, and *Phytophthora capsici*. Compared with the blank control group, the control effect is over 50%.

The above embodiments only describe the preferred mode of the invention, but do not limit the scope of the invention. On the premise of not departing from the design spirit of the invention, various modifications and improvements made by ordinary technicians in the field to the technical scheme of the invention shall fall into the protection scope determined by the claims of the invention.

What is claimed is:

1. A method of preventing, treating or controlling soil-borne diseases of plants by using a biocontrol agent, comprising:
    performing root irrigation to plants when being transplanted, by using the biocontrol agent, wherein the biocontrol agent comprises a YW-1;
    wherein the strain YW-1 is *Myroides odoratimimus*, a preservation number of the strain is CGMCC NO. 20620; and the soil-borne diseases of plants are one or more selected from a group consisting of fusarium wilt of melons, bacterial wilt of tomatoes and peppers, and *Phytophthora capsici*.

2. A method for preparing a biocontrol agent, wherein the biocontrol agent comprises a strain YW-1, the strain YW-1, the strain YW-1 is *Myroides odoratimimus*, a preservation number of the strain is CGMCC NO. 20620; the strain YW-1 is cultured in a Luria-Bertani (LB) culture medium, and then bacterial cells are collected and diluted with sterilized water to prepare the with water to prepare the biocontrol agent with a final concentration of $1\times10^7$ colony-forming units per milliliter (CFU/mL).

3. The method according to claim 2, wherein after culturing the biocontrol strain YW-1 in the LB culture medium, a bacterial suspension is obtained and has an initial concentration of viable bacterial cells of $1\times10^9$-$1\times10^{10}$ CFU/mL.

* * * * *

SEQUENCE LISTING

<160> NUMBER OF SEQ ID NOS: 1

<210> SEQ ID NO 1
<211> LENGTH: 1557
<212> TYPE: DNA
<213> ORGANISM: Artificial Sequence
<220> FEATURE:
<223> OTHER INFORMATION: 16S rDNA sequence of strain YW-1

<400> SEQUENCE: 1

```
gtgaattcga gctcggtacc cggggatcct ctagagatta gagtttgatc agggctcagg      60
atgaacgcta gcggcaggcc taacacatgc aagtcgaggg gtagaagaag cttgcttttt     120
tgagaccggc gcacgggtga gtaacgcgta tgcaacctac cttatacagg ggaatagccc     180
gaagaaattc ggattaatgc tccatggttt atcgatatgg catcgtattg ataataaaga     240
tttatcggta taagatgggc atgcgtatca ttagctagtt ggtgtggtaa cggcatacca     300
aggcaacgat gattaggggt cctgagaggg agatccccca cactggtact gagacacgga     360
ccagactcct acgggaggca gcagtgagga atattggtca atggaggcaa ctctgaacca     420
gccatgccgc gcgcaggatg acggtcctat ggattgtaaa ctgcttttgt acaggaagaa     480
acctccctac gagtagggac ttgacggtac tgtaagaata aggatcggct aactccgtgc     540
cagcagccgc ggtaatacgg aggatccgag cgttatccgg aattattggg tttaaagggt     600
tcgtaggcgg ctttgtaagt cagtggtgaa atttcctagc ttaactagga cactgccatt     660
gatactgcag agcttgaata atatggaagt aactagaata tgtagtgtag cggtgaaatg     720
cttagatatt acatggaata ccaattgcga aggcaggtta ctacgtattt attgacgctg     780
atgaacgaaa gcgtggggag cgaacaggat tagatacccT ggtagtccac gccgtaaacg     840
atggatacta gctgttcggt tttcggactg agtggctaag cgaaagtgat aagtatccca     900
cctggggagt acgttcgcaa gaatgaaact caaaggaatt gacggggggcc cgcacaagcg     960
gtggagcatg tggtttaatt cgatgatacg cgaggaacct taccagggct taaatgtaga    1020
ttgacagatt tggaaacaga tttttcttcg gacaatttac aaggtgctgc atggttgtcg    1080
tcagctcgtg ccgtgaggtg tcaggttaag tcctataacg agcgcaaccc ctattgttag    1140
ttaccagcgc gtagtggcgg ggactctagc aagactgccg gtgcaaaccg tgaggaaggt    1200
ggggatgacg tcaaatcatc acggccctta cgtcctgggc tacacacgtg ctacaatggc    1260
aagtacagaa agcagctacc tggcaacagg atgcgaatct ccaaagcttg tctcagttcg    1320
gattggagtc tgcaactcga ctctatgaag ctggaatcgc tagtaatcgg atatcagcca    1380
```

-continued

```
tgatccggtg aatacgttcc cgggccttgt acacaccgcc cgtcaagcca tggaagctgg    1440
gggtacctga agtcagtgac cgcaaggagc tgcctagggt aaaactagta actagggcta    1500
agtcgtaaca aggtatccgt agaatcgtcg acctgcaggc atgcaagctt ggcgtaa       1557
```